(12) United States Patent
Riegle

(10) Patent No.: US 7,604,009 B1
(45) Date of Patent: Oct. 20, 2009

(54) PORTABLE FLOSSING APPARATUS

(76) Inventor: Steven M. Riegle, 4975 Enchanted Oaks Dr., College Station, TX (US) 77845

( * ) Notice: Subject to any disclaimer, the term of this patent is extended or adjusted under 35 U.S.C. 154(b) by 406 days.

(21) Appl. No.: 11/750,723

(22) Filed: May 18, 2007

(51) Int. Cl.
*A61C 15/00* (2006.01)
(52) U.S. Cl. .......................................... 132/322; 15/23
(58) Field of Classification Search ................ 132/321, 132/322, 323, 328, 329; 15/23, 28
See application file for complete search history.

(56) References Cited

U.S. PATENT DOCUMENTS

| | | | | |
|---|---|---|---|---|
| 3,802,420 A | * | 4/1974 | Moffat et al. | 601/114 |
| 4,083,579 A | * | 4/1978 | Basey et al. | 280/650 |
| 5,217,031 A | | 6/1993 | Santoro | |
| 5,613,508 A | | 3/1997 | Bushman | |
| 5,640,979 A | * | 6/1997 | Trenary | 132/73.6 |
| 7,465,359 B2 | * | 12/2008 | Vives-Martinez | 134/21 |

* cited by examiner

*Primary Examiner*—Robyn Doan
*Assistant Examiner*—Rachel R Steitz
(74) *Attorney, Agent, or Firm*—Crossley Patent Law; Mark A. Crossley

(57) ABSTRACT

The portable battery powered flossing apparatus provides interchangeable rotating floss wheels. Floss wheels are provided with varying degrees of bristle stiffness and in varying diameters. The narrow top of the crown and crown mate provide for even small floss wheels to have access to oral areas as needed. Floss wheels are easily installed, removed, and therefore substituted, one for another. The bristles of the floss wheels are far more long lived than is dental floss. The bristles provide for cleaning between teeth without the age-old problems of typical dental floss. The bristles also provide teeth cleaning. The removable cap is provided for keeping the top of the apparatus and any installed floss wheel clean. The design provides for easy sanitization.

3 Claims, 3 Drawing Sheets

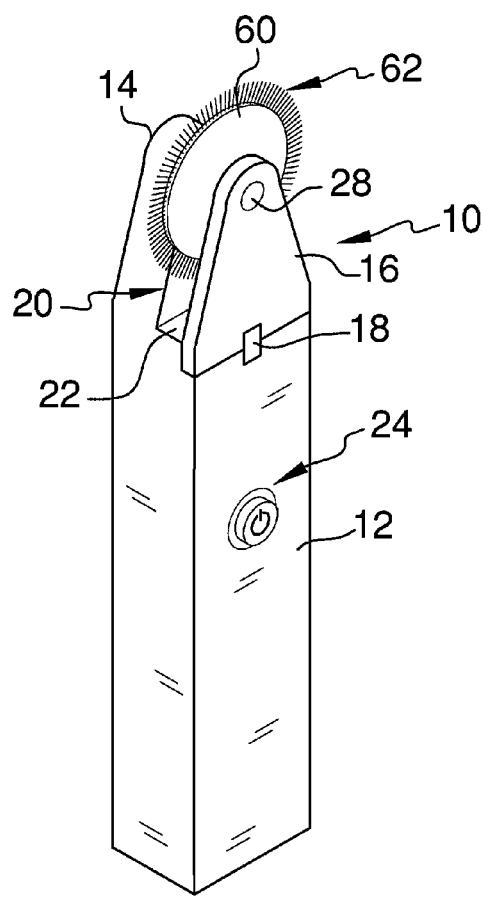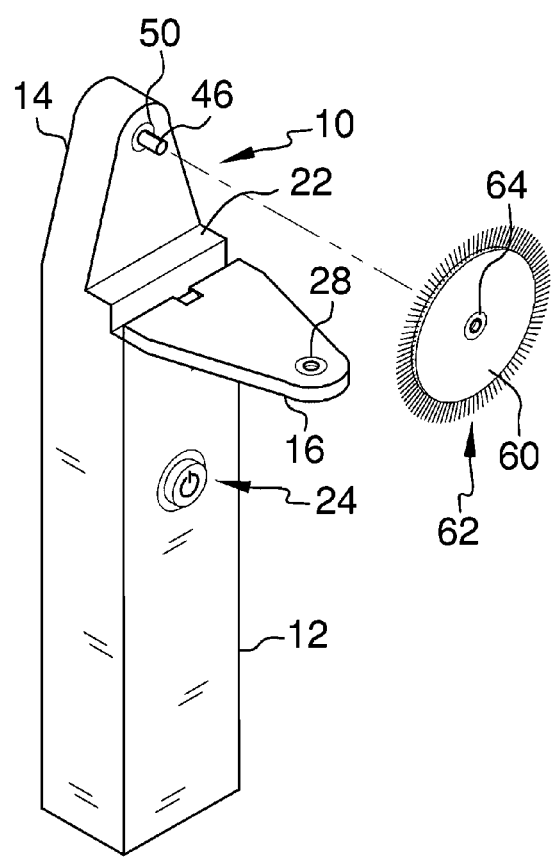
FIG. 1
FIG. 2

PORTABLE FLOSSING APPARATUS

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

Tooth decay and gum problems can often be avoided by regular flossing. A plurality of flosses, flossing devices, and flossing aids have been proposed and provided in the prior art. Typically such devices include the use of typical floss. Typical string floss is abraded and destroyed with use, and must therefore be replenished. In using typical floss in bare-handed style, replenishment involves simply discarding the used floss and grasping the new. With devices which use typical floss, even those which are motorized for moving the floss between teeth, the floss must be replaced often. Frequent replacement of floss, therefore, is a continual problem and inconvenience. What is needed is a motorized device which cleans between teeth without need for passing rapidly degraded floss through the teeth. The device should be compact, portable, and the flossing materials easily replaced, although less frequently so than typically used floss. The device should also be easily sanitized. The present apparatus provides this device.

FIELD OF THE INVENTION

The portable flossing apparatus relates to dental hygiene and flossing, and more especially to a portable motorized device which provides a floss wheel.

DESCRIPTION OF THE PRIOR ART

Prior related art does not provide the advantages of the present apparatus. For example, U.S. Pat. No. 5,217,031 issued to Santoro on 1993 Jun. 8 teaches a motor-driven apparatus which uses typical dental floss. The replacement of the floss, as noted above, is inconvenient and frequently required. U.S. Pat. No. 5,613,508 issued to bushman on 1997 Mar. 25 teaches a dental floss apparatus which, again, uses typical floss and is therefore subjected to the above-listed problems. U.S. patent application Ser. No. 005/000537A1 issued to Junkins on 2005 Jan. 6 teaches a vibratory cleaning devices and methods which uses typical floss and therefore is limited within the above-listed constraints.

While the above-described devices fulfill their respective and particular objects and requirements, they do not describe a portable flossing apparatus that provides for the advantages of the present portable flossing apparatus. In this respect, the present portable flossing apparatus substantially departs from the conventional concepts and designs of the prior art. Therefore, a need exists for an improved portable flossing apparatus.

SUMMARY OF THE INVENTION

The general purpose of the portable flossing apparatus, described subsequently in greater detail, is to provide a portable flossing apparatus which has many novel features that result in an improved portable flossing apparatus which is not anticipated, rendered obvious, suggested, or even implied by prior art, either alone or in combination thereof.

To attain this, the portable flossing apparatus is ideally about 4 inches long and an inch in width. Various embodiments with different battery configurations are provided, some even more narrow for convenience in transport and use. The battery powered apparatus provides interchangeable floss wheels. Floss wheels are provided with varying degrees of bristle stiffness. Floss wheels are provided in varying diameters. The narrow top of the crown and crown mate provide for even small floss wheels to have access to oral areas as needed. Floss wheels are easily installed, removed, and therefore substituted, one for another. The bristles of the floss wheels are far more long lived than is dental floss. The bristles provide for cleaning between teeth without the age-old problems of typical dental floss. The bristles also provide teeth cleaning. The cap is provided for keeping the top of the apparatus and any installed floss wheel clean when the apparatus is not in use.

Thus has been broadly outlined the more important features of the improved portable flossing apparatus so that the detailed description thereof that follows may be better understood and in order that the present contribution to the art may be better appreciated.

An object of the portable flossing apparatus is to be compact.

Another object of the portable flossing apparatus is to highly portable.

A further object of the portable flossing apparatus is to avoid the use of typical dental floss.

An added object of the portable flossing apparatus is to provide easy floss wheel interchangeability.

And, an object of the portable flossing apparatus is to provide for easy sanitization.

A further object of the portable flossing apparatus is to provide for slippage of the floss wheel-to-axle engagement under conditions of excessive rotational resistance.

Additionally, an object of the portable flossing apparatus is to provide for slippage between the motor pulley and slave pulley under conditions of excessive rotational resistance encountered by the axle.

These together with additional objects, features and advantages of the improved portable flossing apparatus will be readily apparent to those of ordinary skill in the art upon reading the following detailed description of presently preferred, but nonetheless illustrative, embodiments of the improved portable flossing apparatus when taken in conjunction with the accompanying drawings.

In this respect, before explaining the current embodiments of the improved portable flossing apparatus in detail, it is to be understood that the portable flossing apparatus is not limited in its application to the details of construction and arrangements of the components set forth in the following description or illustration. Those skilled in the art will appreciate that the concept of this disclosure may be readily utilized as a basis for the design of other structures, methods, and systems for carrying out the several purposes of the improved portable flossing apparatus. It is therefore important that the claims be regarded as including such equivalent constructions insofar as they do not depart from the spirit and scope of the portable flossing apparatus. It is also to be understood that the phraseology and terminology employed herein are for purposes of description and should not be regarded as limiting.

BRIEF DESCRIPTION OF THE DRAWINGS

FIG. 1 is a perspective, fully assembled view.
FIG. 2 is a perspective view illustrating floss wheel removability.

DETAILED DESCRIPTION OF THE DRAWINGS

Figure 3:
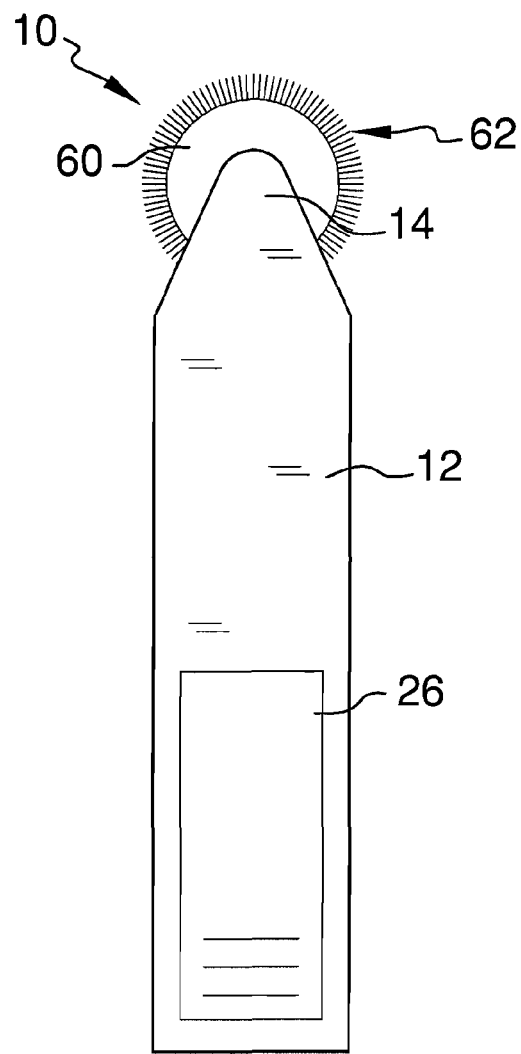
FIG. 3 is back elevation view.
Figure 4:
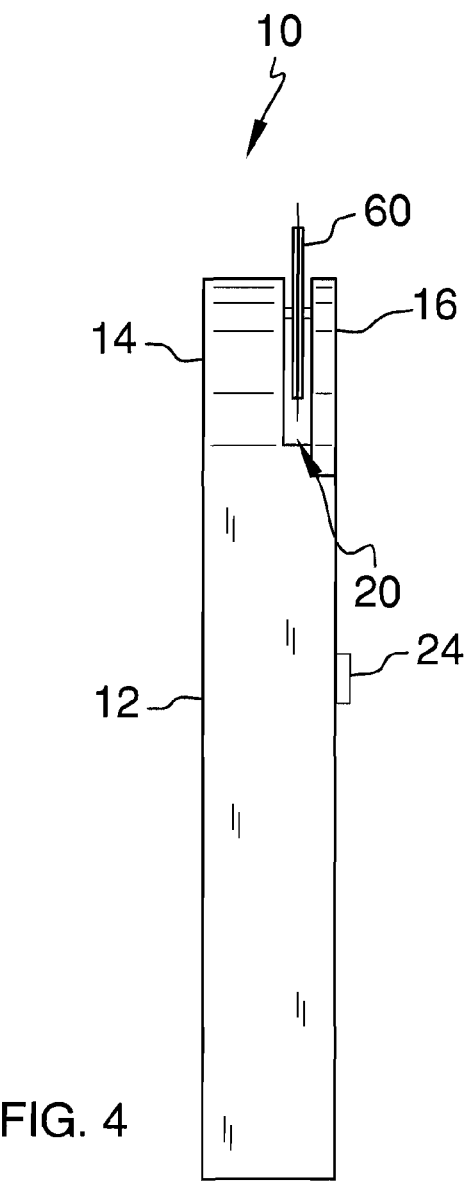
FIG. 4 is side elevation view.
Figure 5:
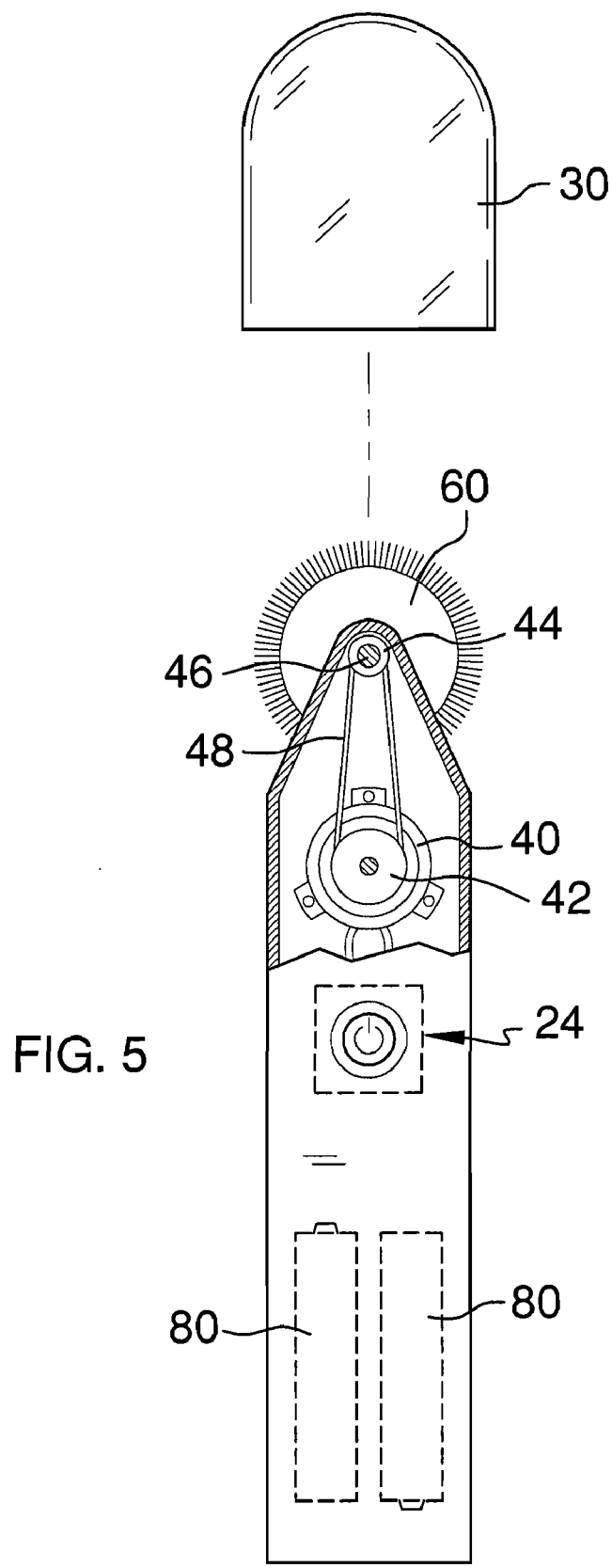
FIG. 5 is a back, partial cross sectional view.

With reference now to the drawings, and in particular FIGS. 1 through 5 thereof, the principles and concepts of the portable flossing apparatus generally designated by the reference number 10 will be described.

With reference to FIGS. 1 through 5, the portable flossing apparatus 10 comprises a parallelepiped body 12. The body 12 has a first end, a second end, and a length therebetween. The battery compartment is disposed within the body 12, proximal to the second end. The removable battery compartment cover 26 is provided for containing a battery 80 or batteries 80 within. The motor 40 is disposed within the body 12 proximal to the first end of the body 12. The motor pulley 42 is disposed within the body 12. The motor pulley 42 is affixed to the motor 40. The externally accessible on/off 24 is disposed within the body 12. The on/off 24 is in communication with the battery compartment and the motor 40. The triangular shaped crown 14 is disposed atop the first end of the body 12. The crown mate 16 is movably positionable to a position in alignment with the crown 12. The crown mate 16 is further pivotally positionable with the top of the crown mate 16 away from the crown 12. With the crown mate 16 positioned in alignment with and proximal to the crown 14, the wheel channel 20 is formed between the crown 14 and the crown mate 16. The shelf 22 is disposed at the bottom of the wheel channel 20. The wheel channel 20 and shelf 22 provide a partial cover for a portion of the rotatable floss wheel 60. The bushing 28 is disposed proximal to the top of the crown mate 16. The retainer 18 is provided for selectively retaining the crown mate 16 in a position in alignment with the crown 14. The axle 46 is disposed proximal to a top of the crown 14. The sealed bearing 50 rotatably houses the axle 46. The sealed bearing 50 and the uncluttered channel 20 and shelf 22 provide for ease of sanitization of the apparatus 10. The apparatus 10 top end can be washed and sanitized as needed without fear of invasion of chemical or liquids into the apparatus 10. The slave pulley 44 is disposed within the body 12. The slave pulley 44 is disposed on a one end of the axle 46. The flexible belt 48 is disposed within the body 12. The belt 48 connects the motor pulley 42 to the slave pulley 44. There are offered a plurality of floss wheels 60. Wheels 60 differ by virtue of differing property of bristles 62. Bristles 62 are provided in varying degrees of stiffness. Each floss wheel 60 is provided with an elastomeric engagement 64 within the center of the wheel 60. Pivot of the crown mate 16 provides for removal of a given floss wheel 60 and replacement as needed. The elastomeric engagement 64 has an orifice for receipt of the axle 46. The elastomeric engagement 64 provides a frictional engagement 64 that also provides removable fit to the axle 46. The frictional fit of the engagement 64 also provides a degree of forgiveness as follows. If the floss wheel 60 encounters excessive resistance, the engagement 64 provides for slippage with the axle 46. This is a designed safety factor against mouth injury. Further, the flexible belt 48 provides a degree of safety by allowing slip in cases of excessive resistance against axle 46 rotation. There are thereby provided two safety factors within the apparatus 10, insuring against oral injury.

With respect to the above description then, it is to be realized that the optimum dimensional relationships for the parts of the portable flossing apparatus, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the portable flossing apparatus.

Directional terms such as "front", "back", "in", "out", "downward", "upper", "lower", and the like may have been used in the description. These terms are applicable to the embodiments shown and described in conjunction with the drawings. These terms are merely used for the purpose of description in connection with the drawings and do not necessarily apply to the position in which the portable flossing apparatus may be used. Therefore, the foregoing is considered as illustrative only of the principles of the portable flossing apparatus. Further, since numerous modifications and changes will readily occur to those skilled in the art, it is not desired to limit the portable flossing apparatus to the exact construction and operation shown and described, and accordingly, all suitable modifications and equivalents may be resorted to, falling within the scope of the portable flossing apparatus.

What is claimed is:

1. A portable flossing apparatus comprising:
    a parallelepiped body having a first end, a second end, and a length therebetween;
    a battery compartment within the body, the compartment proximal to the second end;
    a removable battery compartment cover;
    a motor within the body and proximal to the first end of the body;
    a motor pulley within the body, the motor pulley disposed on the motor;
    an externally accessible on/off within the body; the on/off in communication with the battery compartment and the motor;
    a triangular shaped crown disposed atop the first end of the body;
    a crown mate movably positionable to a position in alignment with the crown;
    a wheel channel formed between the crown and the crown mate;
    a shelf at a bottom of the wheel channel;
    a bushing proximal to a top of the crown mate;
    a retainer for selectively retaining the crown mate in the position in alignment with the crown;
    an axle disposed proximal to a top of the crown;
    a sealed bearing rotatably housing a part of the axle;
    a slave pulley within the body, the slave pulley disposed on a one end of the axle;
    a flexible belt within the body, the belt connecting the motor pulley to the slave pulley;
    a floss wheel having a plurality of bristles on an outer diameter of the wheel;
    an elastomeric engagement within a center of the floss wheel, the engagement for removable fit to the axle.

2. The apparatus according to claim 1 further comprising a plurality of rotating floss wheels, each floss wheel having a different property of bristles.

3. The apparatus according to claim 2 further comprising a plurality of floss wheel diameters.

* * * * *